(12) United States Patent
Roberts et al.

(10) Patent No.: US 11,384,440 B1
(45) Date of Patent: Jul. 12, 2022

(54) STRUCTURALLY ALTERED GAS MOLECULE PRODUCED FROM WATER AND METHOD OF GENERATION THEREOF

(71) Applicant: HydraVes Technologies Inc., Mesquite, NV (US)

(72) Inventors: Jared Roberts, Grand Junction, CO (US); Gene Dedick, Grand Junction, CO (US)

(73) Assignee: HYDRAVES TECHNOLOGIES INC., Mesquite, NV (US)

( * ) Notice: Subject to any disclaimer, the term of this patent is extended or adjusted under 35 U.S.C. 154(b) by 0 days.

(21) Appl. No.: 17/487,613

(22) Filed: Sep. 28, 2021

(51) Int. Cl.
| | |
|---|---|
| *C01B 5/02* | (2006.01) |
| *C25B 1/04* | (2021.01) |
| *C25B 15/027* | (2021.01) |
| *B01J 19/12* | (2006.01) |
| *C01B 5/00* | (2006.01) |

(52) U.S. Cl.
CPC ............. *C25B 1/04* (2013.01); *B01J 19/12* (2013.01); *C01B 5/00* (2013.01); *C25B 15/027* (2021.01)

(58) Field of Classification Search
CPC .................................. C01B 5/00; C01B 5/02
See application file for complete search history.

(56) References Cited

U.S. PATENT DOCUMENTS

| | | | |
|---|---|---|---|
| 10,626,036 B1 * | 4/2020 | Guoin | A61K 33/00 |
| 2017/0368528 A1 * | 12/2017 | Gourley | C25B 9/05 |

* cited by examiner

*Primary Examiner* — Zulmariam Mendez
(74) *Attorney, Agent, or Firm* — Georgiy L. Khayet (57) ABSTRACT

A method for generating a structurally altered gas molecule from water. An example method includes placing an electrolyte solution in a chemical reaction chamber, adding purified water to the chemical reaction chamber, and applying a focused magnetic field and an electric field to a mixture of the purified water and the electrolyte solution to cause generation of the structurally altered gas molecule from the purified water. The structurally altered gas molecule is a combination of two parts of hydrogen and one part of oxygen. The structurally altered gas molecule has a hydrogen-oxygen-hydrogen bond angle between 94 degrees and 104 degrees and hydrogen-oxygen bond length between 0.95 Angstrom and 1.3 Angstrom. The structurally altered gas molecule is stable at a pressure exceeding 300 pounds per square inch gauge.

13 Claims, 11 Drawing Sheets

Table 1. GC-MS Peak Areas

| Gas | H₂O | N₂ | O₂ |
|---|---|---|---|
| Amu | 18 | 28 | 32 |
| | Peak Area Count | | |
| Blank Air 1 | 114,519,186 | 7,613,794,922 | 4,054,893,405 |
| WA Sample | 148,481,381 | 7,876,575,862 | 4,246,703,524 |
| Blank air 2 | 111,381,950 | 7,979,823,940 | 4,274,157,002 |
| WB Sample | 109,386,595 | 7,921,595,391 | 4,117,905,056 |

Table 2. GC-MS Peak Area Percentage

| Gas | H₂O | N₂ | O₂ |
|---|---|---|---|
| Amu | 18 | 28 | 32 |
| | Peak Area % | | |
| Blank Air 1 | 0.97 | 64.62 | 34.41 |
| WA Sample | 1.21 | 64.18 | 34.61 |
| Blank Air 2 | 0.90 | 64.53 | 34.57 |
| WB Sample | 0.90 | 65.20 | 33.90 |

STRUCTURALLY ALTERED GAS MOLECULE PRODUCED FROM WATER AND METHOD OF GENERATION THEREOF

TECHNICAL FIELD

This disclosure relates to an apparatus and methods for generating a structurally altered gas molecule from water.

BACKGROUND

Infusion liquids with gases is widely used to alter or improve properties of the liquids, for example, to change their pH levels and oxidation/reduction potentials. Gas-infused liquids are used in many applications, such as polymerization, salt formation, crystallization, and others. In addition, the produced gas molecule can be used as clean fuel. When infused in other fuels, the gas molecule can be useful in the production and treatment of various fuels to improve power and efficiency and reduce emissions. Moreover, the produced gas molecule can provide numerous health benefits to many living forms of fauna and flora and can be used to enhance the manufacturing and application of paints and many other manufactured and applied products.

SUMMARY

This section is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

This disclosure relates to a method for generating a structurally altered gas molecule from water. The method may include adding an electrolyte solution to a chemical reaction chamber. The method may further include adding water to the chemical reaction chamber. The method may further include applying a focused magnetic field and an electric field to a mixture of the purified water and the electrolyte solution to cause generation of the structurally altered gas molecule from the purified water. The structurally altered gas molecule can be a combination of two parts of hydrogen and one part of oxygen. The structurally altered gas molecule may have a hydrogen-oxygen-hydrogen bond angle between 94 degrees and 104 degrees and hydrogen-oxygen bond length between 0.95 Angstrom and 1.3 Angstrom.

The temperature in the chemical reaction chamber can be from 60 degrees to 120 degrees in Fahrenheit. The pressure in the chemical reaction chamber can be from 1 atmosphere to 40 pounds per square inch gauge. The electrolyte solution can be made using a mixture of a hydroxide salt and an acid salt. The focused magnetic field can be generated by earth magnets.

The density of the structurally altered gas molecule relative to a dry air can be from 41.18% to 42% at standard temperature and pressure (STP). The structurally altered gas molecule can be stable at a pressure exceeding 300 pounds per square inch gauge.

The oxidation/reduction potential of a solution of the structurally altered gas molecule and the purified water can be −50 to −360 millivolts (mV) and pH of the solution can range from 6.1 to 6.8. The oxidation/reduction potential and the pH can remain stable for at least 30 days after the solution is placed in closed insoluble vessel.

When the structurally altered gas molecule is dissolved in water having two parts per million (ppm) of total dissolved solids (TDS), the TDS can be reduced by 50% or to one ppm using standard conductivity measurement. The infrared spectrum of the structurally altered gas molecule includes a peak at 600 inverse centimeters. The hydrogen bonding of the structurally altered gas can be neutralized. The hydrogen bonding in water infused by the structurally altered gas molecule can be neutralized.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

DETAILED DESCRIPTION OF EXAMPLE EMBODIMENTS

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Generally, the embodiments of this disclosure are concerned with methods for generating a structurally altered gas molecule from water. An example method includes placing an electrolyte solution in a chemical reaction chamber. The method may further include adding water to the chemical reaction chamber. The method may also include applying a focused magnetic field and an electric field to a mixture of the purified water and the electrolyte solution to cause generation of the structurally altered gas molecule from the purified water. The structurally altered gas molecule can be a combination of two parts of hydrogen and one part of oxygen. The structurally altered gas molecule may have a hydrogen-oxygen-hydrogen bond angle between 94 degrees and 104 degrees and hydrogen-oxygen bond length between 0.95 Angstrom and 1.3 Angstrom.

The structurally altered gas molecule can be used in different applications. In one application, the produced structurally altered gas molecule can be used as a fuel itself and enhance the performance of other fuels efficiency while minimizing the undesirable emissions. Water infused with the structurally altered gas molecule can be used as a hydration source to improve the general cellular function of living organisms. In another application, the water infused with the structurally altered gas molecule can be used in watering plants to increase plant growth. In yet another application, the structurally altered gas molecule can be used in manufacturing of water-based paints to impart structural changes on the paint. This may allow enhancing uniform dispersion of the paint solids when applied to the surface, improving a flow of the paint out of the sprayer, roller, or brush onto the surface that is painted, and decrease time for drying the paints. Various applications are described in further detail in the Appendix to this Specification. The aforementioned Appendix is incorporated herein by reference for all purposes.

Figure 1:
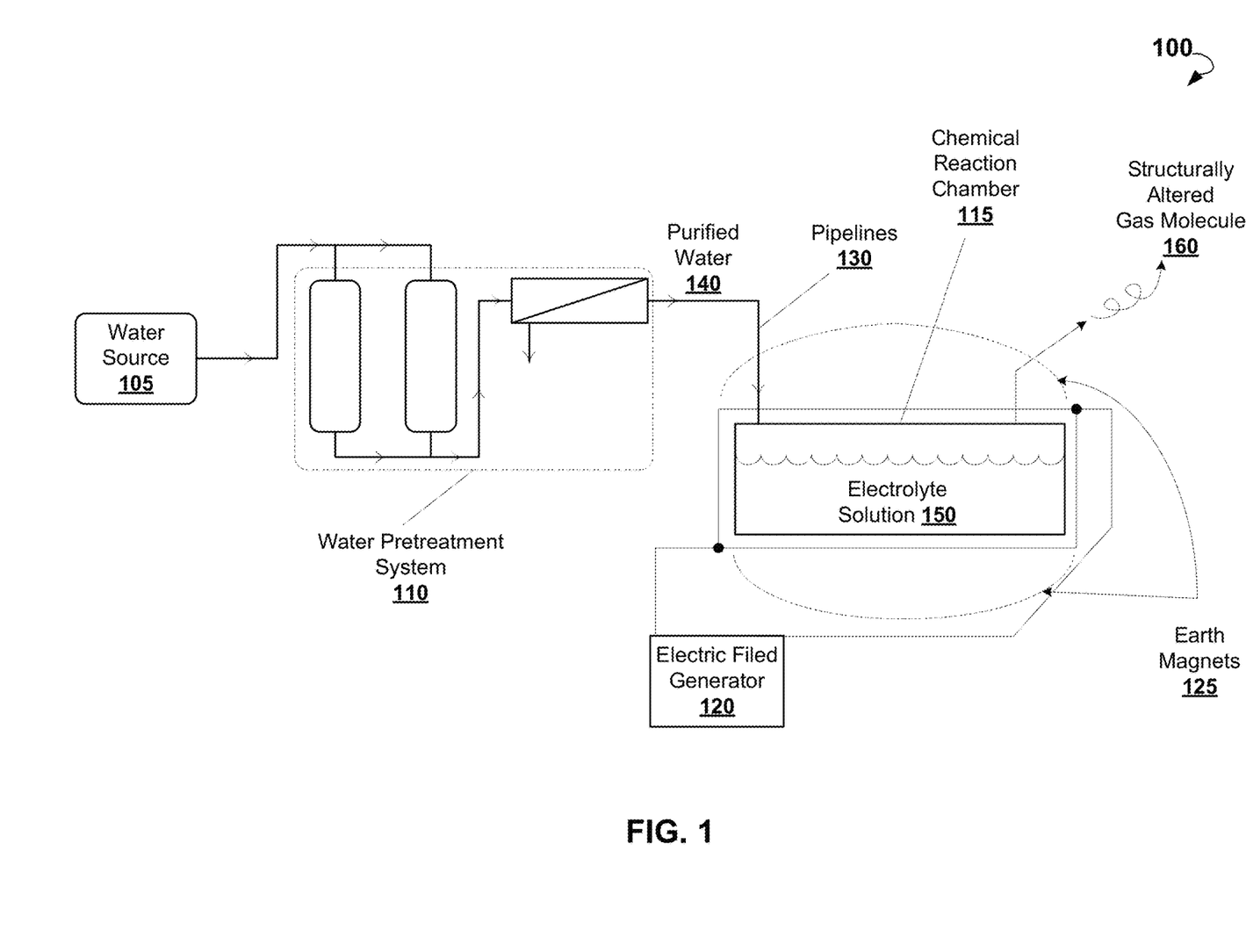
FIG. 1 illustrates an example system for generating a structurally altered gas molecule, according to an example embodiment.

FIG. 1 illustrates an example system 100 for generating a structurally altered gas molecule, according to an example embodiment. The system 100 may include a water source 105, a water pretreatment system 110, a chemical reaction chamber 115, an electric field generator 120, earth magnets 125, and pipelines 130. The system may also include pressure regulators. The electric field generator 120 may include an electrical inverter and solar panels.

The water source 105 may provide water as a raw material for generating the gas molecule product. The water pretreatment system 110 may prepare the water for the chemical reaction chamber 115. The water pretreatment system 110 may include a filtration system, an absorption system, and a purification system to produce the purified water 140.

The chemical reaction chamber 115 may contain an electrolyte solution 150. The electrolyte solution 150 can be made using a mixture of a hydroxide salt and an acid salt. The purified water 140 can be provided to the chemical reaction chamber 115. The earth magnets 125 may generate a permanent focused magnetic field. The electrical field generator 120 may generate an electromagnetic field. The focused magnetic field and the electrical field may drive chemical reaction that generates the structurally altered gas molecule 160 from the purified water supplied into the chemical reaction chamber 115. The electrolyte solution 150 may provide a medium for the focused magnetic field to align and impart energy of the focused magnetic field on the purified water mixed in with the electrolyte solution and, thereby, chemically generate the structurally altered gas molecule 160 from the purified water 140. The temperature in the chemical reaction chamber 115 can be from 60 degrees to 120 degrees in Fahrenheit. The pressure in the chemical reaction chamber 115 can be from 1 atmosphere to 40 pounds per square inch gauge (psig).

The structurally altered gas molecule 160 can be 99.9% hydrogen and oxygen combination in two parts of hydrogen to one part of oxygen ratio at the standard temperature of 68 degrees of Fahrenheit and pressure of 1 atmosphere (STP). The structurally altered gas molecule 160 may have the O—H bond length between 0.95 and 1.3 angstroms and the H—O—H bond angle between 94 degrees and 104 degrees.

The molecular weight of the structurally altered gas molecule 160 can be between 12.14 and 12.18 atomic mass units (AMUs) at STP. In comparison, the molecular weight of pure water vapor is 18 AMUs at STP. At STP, the relative density of the structurally altered gas molecule 160 compared to dry air is 41.18%-42.00%. In comparison, relative density of pure water vapor compared to dry air is 62.19%. The structurally altered gas molecule 160 may remain stable at pressure more than 300 psig.

When dissolved in pure water having 2 parts per million (ppm) of total dissolved solids (TDS) at 25 degrees of Celsius, the structurally altered gas molecule 160 may generate an oxidation/reduction potential (ORP) of approximately −50 to −360 mV and a pH of 6.1 to 6.8 in the resulting gas-water mixture. The ORP and pH may remain stable in a closed insoluble vessel for at least 30 days. In comparison, the pure water does not possess a stable negative ORP at a pH below 7.

When dissolved in pure water (2 ppm TDS at 25 degrees of Celsius), the structurally altered gas molecule 160 may reduce the concentration of TDS from 2.0 ppm to 1.0 ppm, i.e., the reduction is 50%. Barring contamination, the concentration of TDS remains stable at 1 ppm in a closed insoluble vessel indefinitely.

The changes in structure and properties of the structurally altered gas molecule 160 are caused by changes in electronic structure of the gas structurally altered molecule 160 due to applying the focused magnetic field and the electrical field to the mixture of the electrolyte solution 150 and purified water 140.

Figure 2:
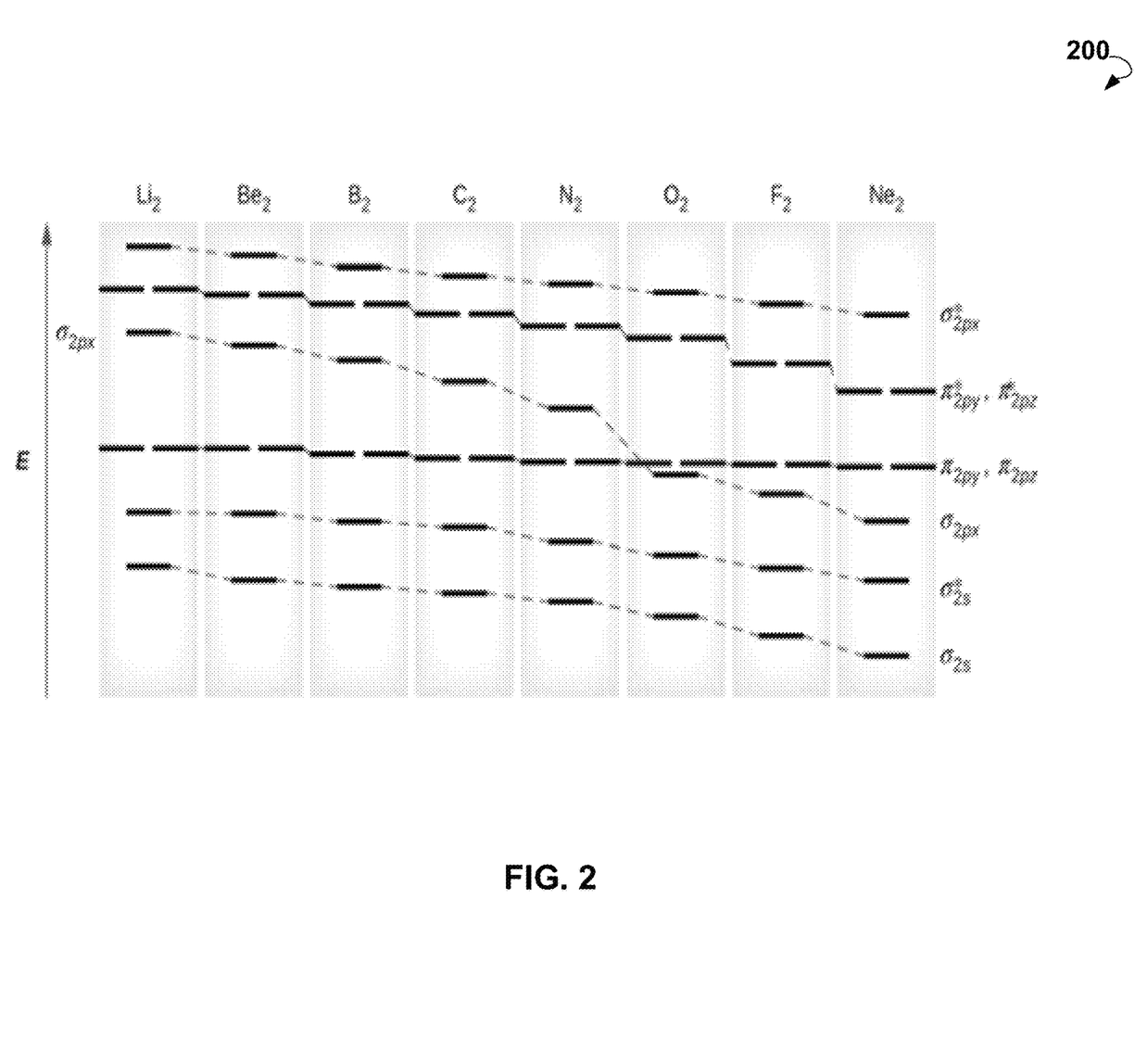
FIG. 2 is a diagram showing energy levels of molecular orbitals of homonuclear diatomic molecules of elements of the second period in the periodic table.

FIG. 2 is a diagram showing energy levels 200 of molecular orbitals of homonuclear diatomic molecules of elements of the second period in the periodic table. In the Molecular Orbital Theory, there is known a phenomenon called σ-π (sigma-pi) mixing. This phenomenon influences existing s and p molecular orbitals by imparting electromagnetic energy. In the case of oxygen, the sigma-2px, pi-2py and pi-2pz orbitals are close enough for the respective stability. Thus, the energy levels of these orbitals can supersede each other with small amounts of focused energy input. The superseding in the energy levels has a direct effect on the molecular wavefunction of a molecule, effective nuclear charge, atomic radius of the oxygen in molecules, and causes significant changes in the molecular structure.

According to the Molecular Orbital Theory, the electrons are delocalized throughout the entire molecule to allow atomic orbitals to form molecular orbitals. This effect allows creating both bonding and anti-bonding interactions for filling orbitals. Accordingly, this allows predicting of the arrangement of electrons in molecules.

The de-localization of electrons and change in energy levels (substantiated by Molecular Orbital Theory as described above) can be imparted by the process described in above with reference to FIG. 1. Application of the focused magnetic field and the electric field on the purified water feedstock in the presence of the electrolyte solution is the driver for the structural changes to purified water feedstock. The structural changes convert the purified water from a liquid form to a gaseous form with a two hydrogen to one oxygen ratio. These structural changes allow molecules of the gaseous form to exist as a stable gas at STP.

The structural changes include changes in the bond angle, bond length and neutralization of hydrogen bonding by deploying sufficient energy to neutralize the hydrogen bonding in the pure water. Structural changes similar to the ones that allow molecules of the same outer valence orbitals with lone pairs of electrons in their structure to exist as both gasses and liquids, are observed in nature. For example, pure water ($H_2O$) with molecular weight of 18.0 g/mol, has a bond angle of 104.5 degrees and an O—H bond length of 0.9572 angstroms and exists as a liquid at STP. Hydrogen sulfide, ($H_2S$), has the same outer valence structure as oxygen and a molecular weight of 34.1, a bond angle of 92.1 degrees and an S—H bond length of 1.34 angstroms. However, in contrast to the pure water, the hydrogen sulfide exists as a gas at STP.

Figure 3:
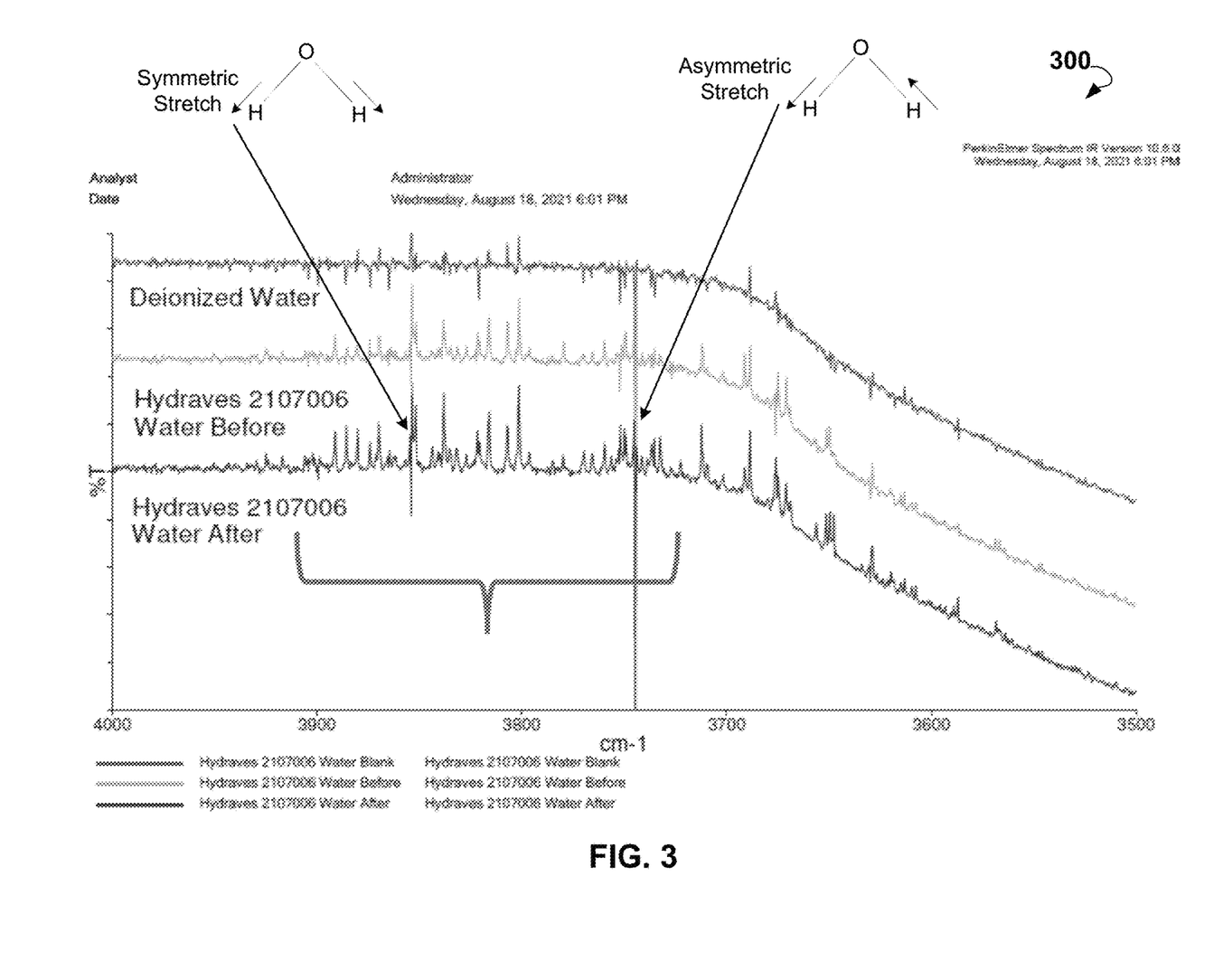
FIGS. 3 and 4 are plots of the Fourier Transform Infrared (FTIR) transmittance spectra of deionized water, a pure water before infusion with the structurally altered gas molecule, and a pure water after infusion with the structurally altered gas molecule.

FIG. 3 is a plot 300 of the Fourier Transform Infrared (FTIR) transmittance spectra of deionized water, a pure water before (WB) infusion with the structurally altered gas molecule, and a pure water after (WA) infusion with the structurally altered gas molecule in the region of 3500-4000 inverse centimeters ($cm^{-1}$).

Figure 4:
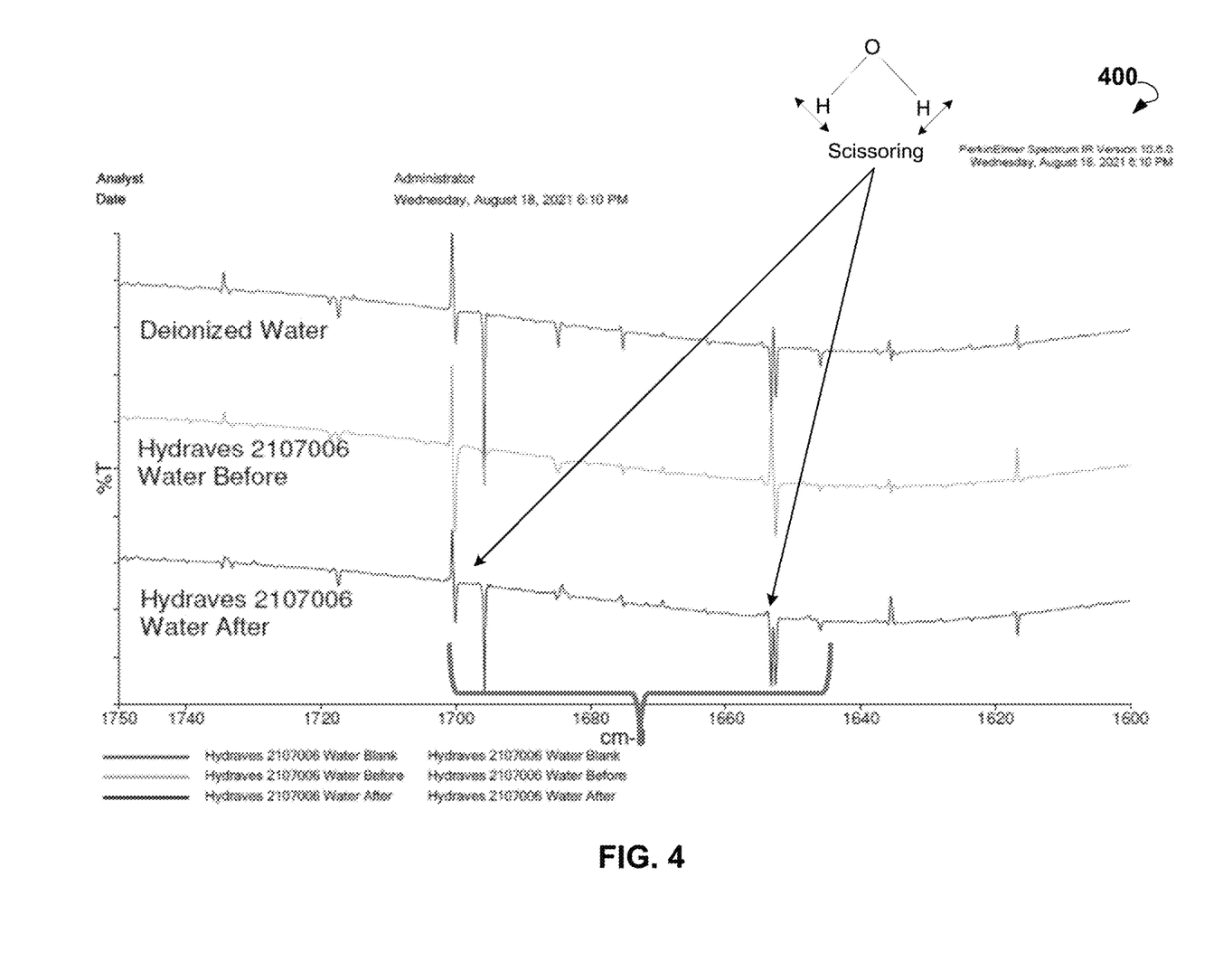

FIG. 4 is a plot 400 of the FTIR transmittance spectra of deionized water, WB, and WA in the region of 1600-1750 $cm^{-1}$. The plots 300 and 400 show differences in bands corresponding to the symmetrical and asymmetrical stretch in bond length and bands corresponding to the bond angle "scissoring".

Figure 5:
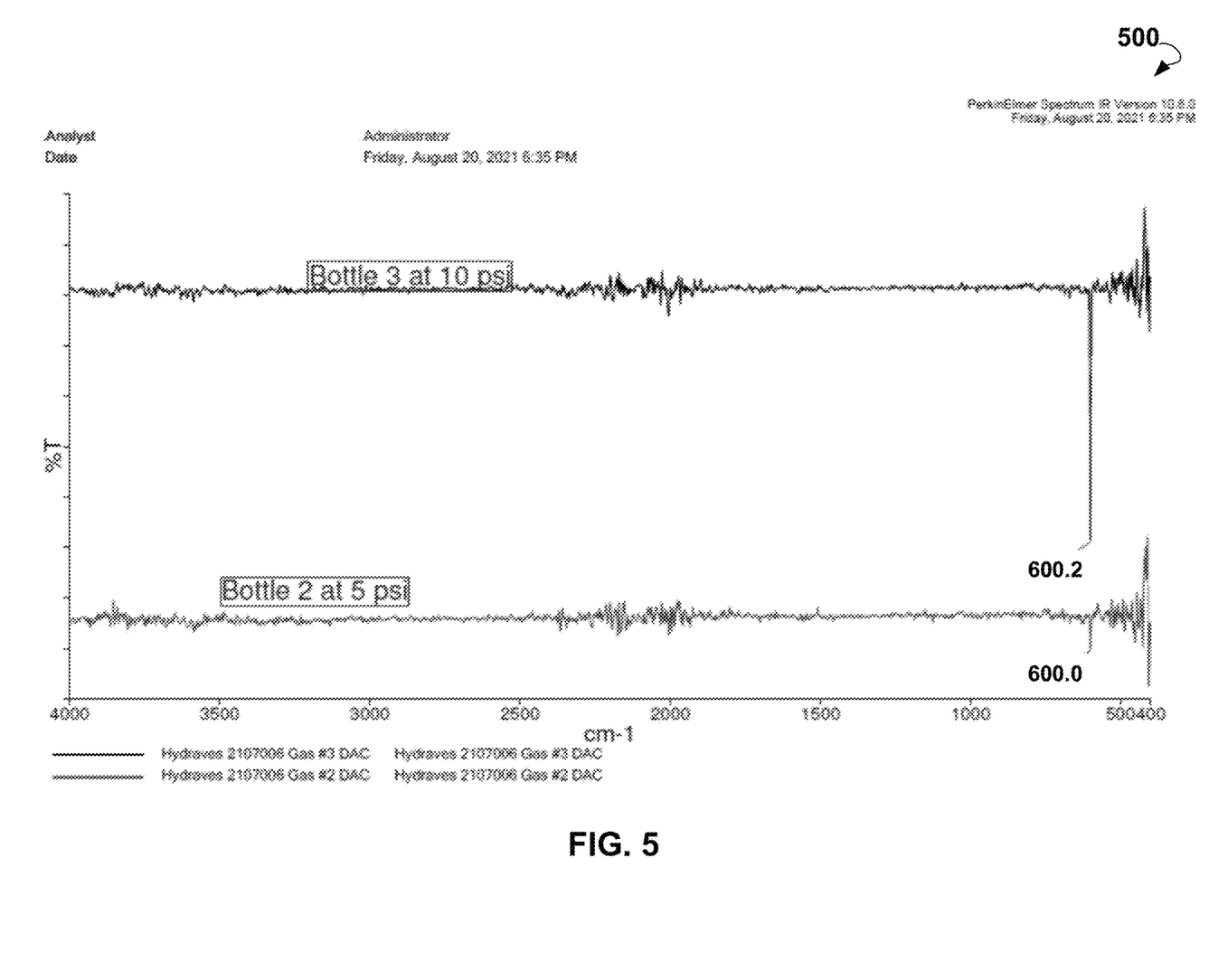
FIG. 5 are plots of FTIR molecular spectra of the structurally altered gas molecule at pressures of 10 per square inch (psi) and 5 psi.

FIG. 5 are plots 500 of FTIR molecular spectra of the structurally altered gas molecule at pressures of 10 per square inch (psi) and 5 psi. The peaks at 600.2 $cm^{-1}$ and 600.0 $cm^{-1}$ in the plots 500 show that the structurally altered gas molecule 160 has a unique structure different from the structure of the pure water vapor. In comparison, an FTIR molecular spectra of the pure water vapor has no peaks in the area around 600 $cm^{-1}$. Additionally, the peaks at 600 $cm^{-1}$ cannot be related to a diatomic gas because the FTIR of divalent gasses does not include peaks. Furthermore, the peaks at 600.2 $cm^{-1}$ and 600.0 $cm^{-1}$ are directly proportional to the observed gas molecule pressures recorded during the analysis. This proportionality substantiates that the peaks at 600.2 $cm^{-1}$ and 600.0 $cm^{-1}$ are caused by the pure structurally altered gas molecule 160 generated by the system 100.

Neutralization of hydrogen bonding in the pure water feedstock allows the resulting gaseous HOH molecule to be released (evaporated) from the chemical reaction chamber 115 via restructuring the pure water in the gaseous form. The neutralization of the hydrogen bond and increase in evaporation is also observed in water that has been infused with structurally altered gas molecule 160.

Figure 6:
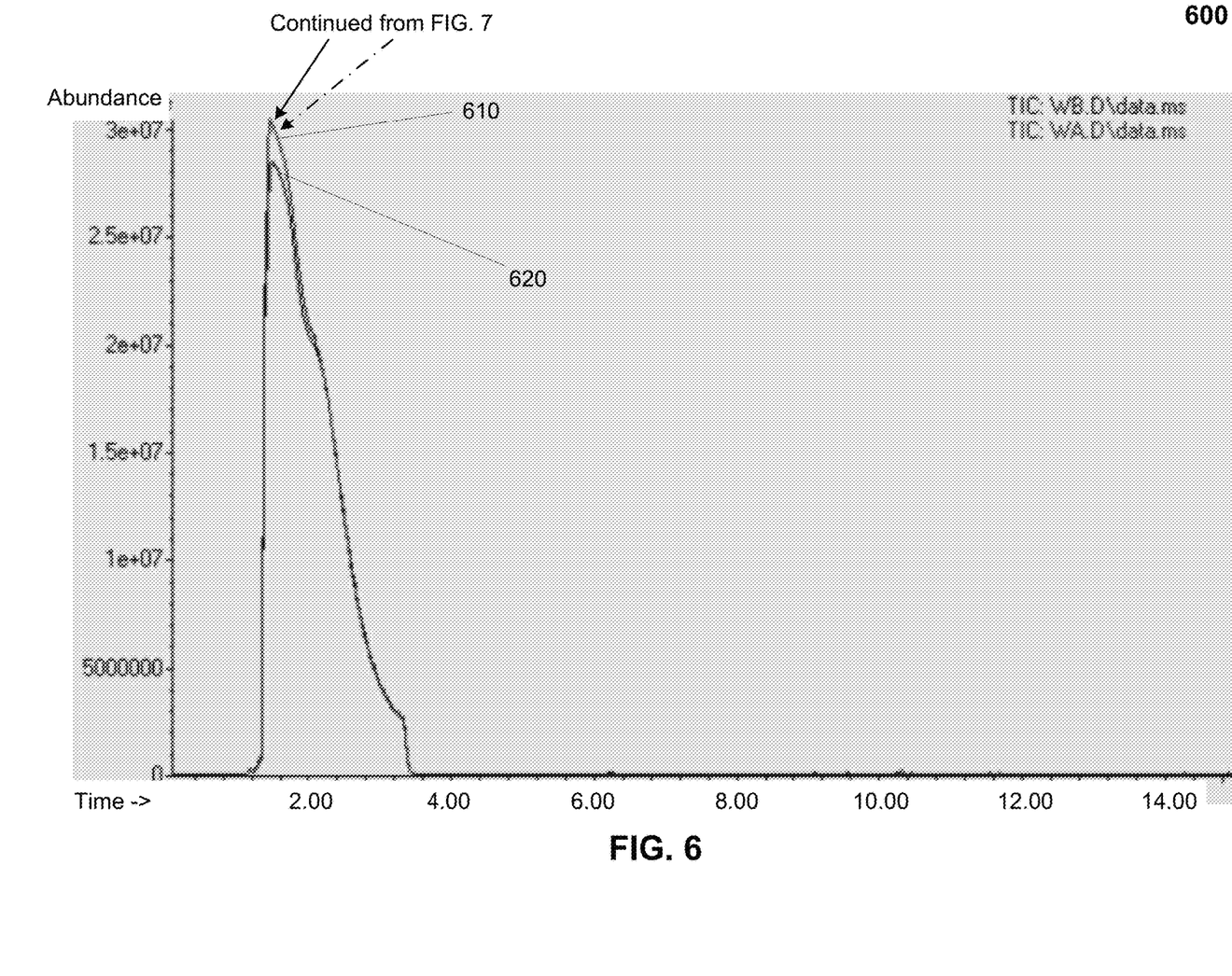
FIG. 6 is plot of a chromatogram of water after infusion with the structurally altered gas molecule and a chromatogram of water before infusion with the structurally altered gas molecule.

FIG. 6 is plot 600 of a chromatogram 610 of the WA infusion with the structurally altered gas molecule and a chromatogram 620 of the WB infusion with the structurally altered gas molecule. The chromatograms 610 and 620 are recorded using gas chromatography-mass spectrometry (GC-MS).

Figure 7:
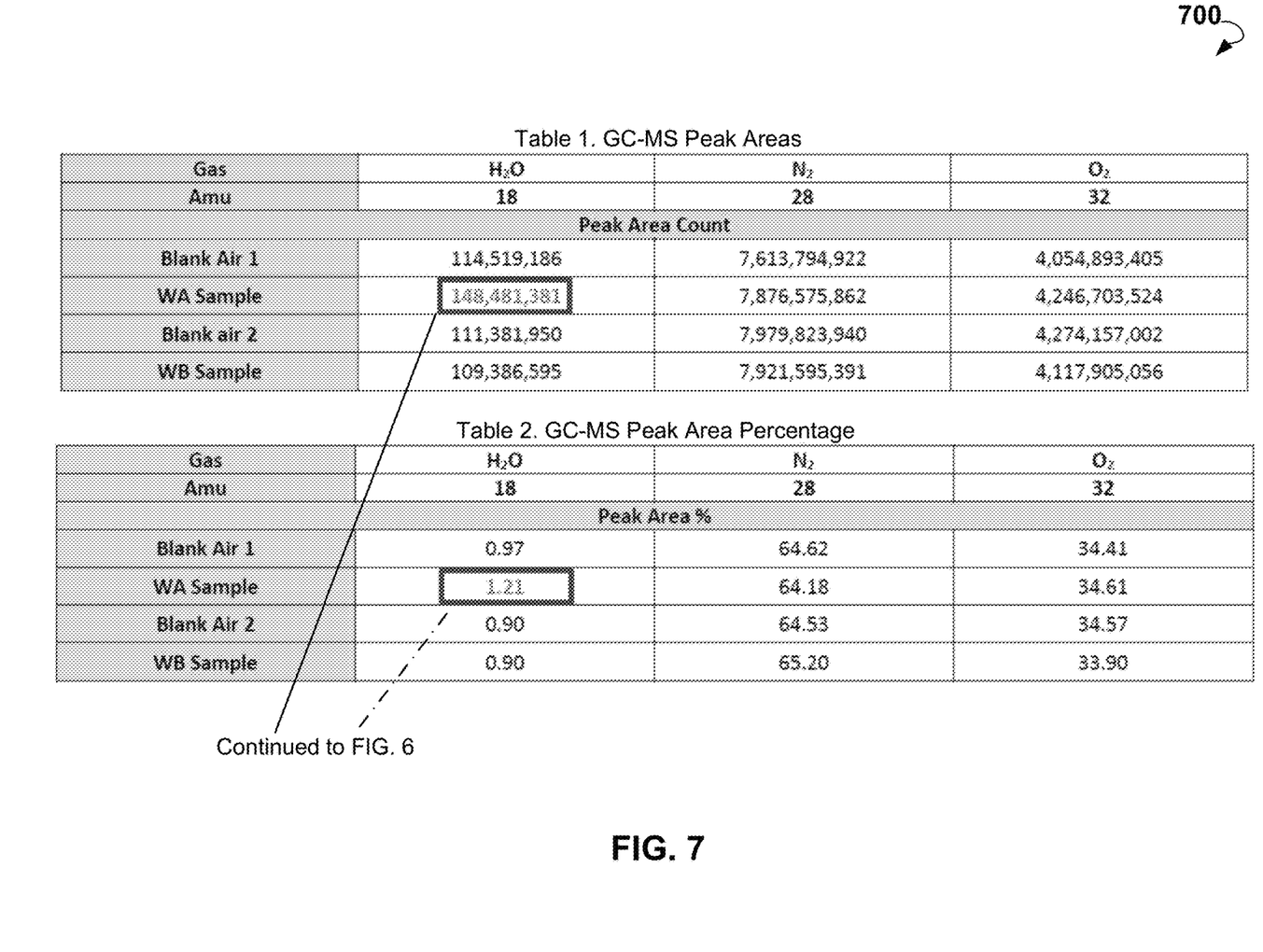
FIG. 7 depicts a table showing peak area counts in the chromatograms shown in FIG. 6 and a table showing percentage of peak area counts in the chromatograms shown in FIG. 6.

FIG. 7 is a diagram 700 that depicts Table 1 showing peak area counts in the chromatograms 610 and 620 shown in FIG. 6 and Table 2 showing percentage of peak area counts in the chromatograms 610 and 620 shown in FIG. 6. The peak area for WA is larger than the peak area for WB. The percentage of the peak area for the WA is also larger than the percentage of the peak area for the WB. The same increase in the peak area is also observed for structurally altered gas molecule 160 as compared to the regular water vapor.

Figure 8:
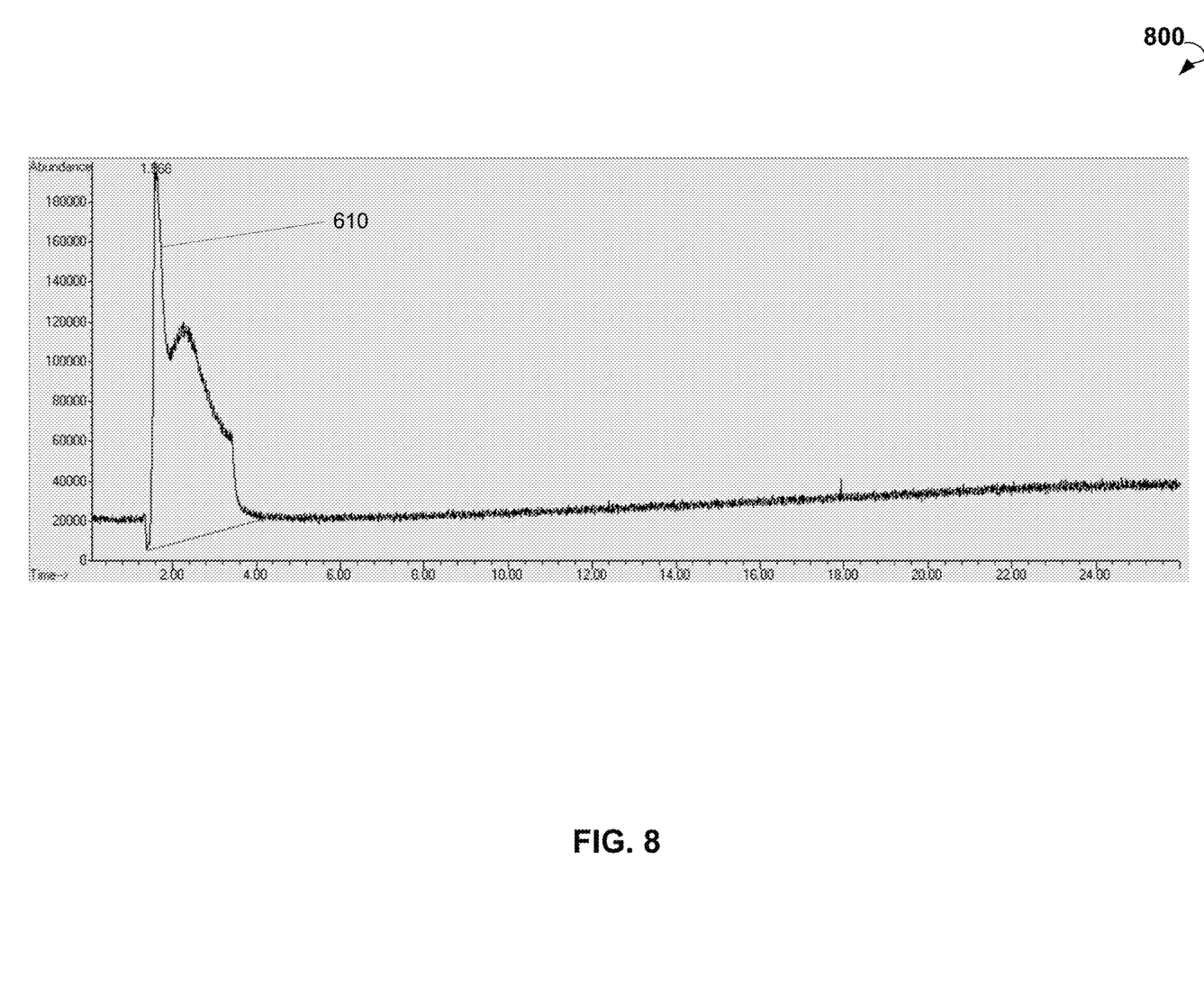
FIG. 8 is an expanded plot of a chromatogram of water after infusion with the structurally altered gas molecule.
Figure 9:
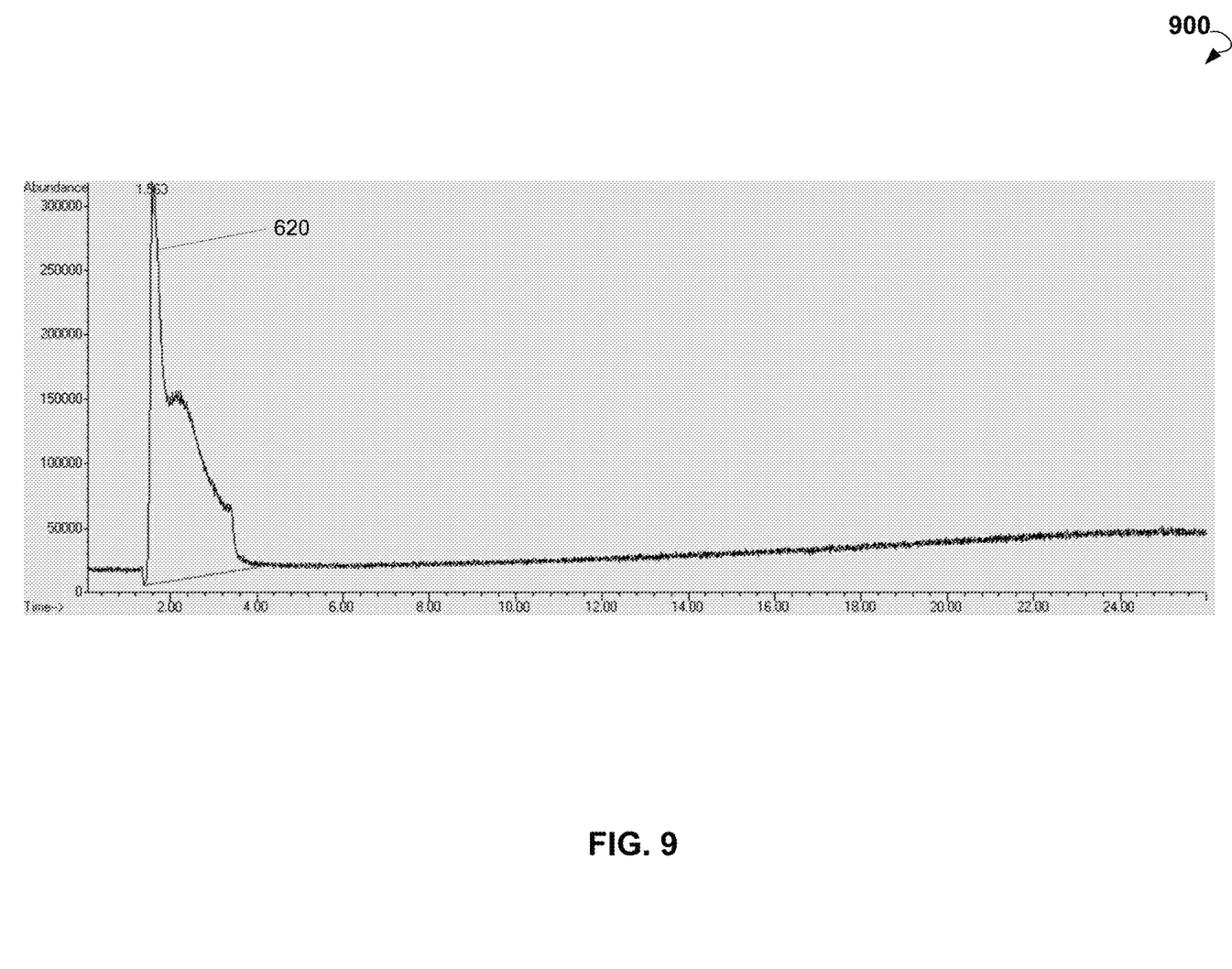
FIG. 9 is an expanded plot of a gas chromatography-mass spectrometry chromatogram of water before infusion with the structurally altered gas molecule.

FIG. 8 shows an expanded plot 800 of the chromatogram 610 and FIG. 9 shows an expanded plot 900 of the chromatogram 620. The first peak in the 1.56 range on the X axis (Time) shows an approximate 40% increase in value of Abundance, (Y axis) from 200,000 to 320,000 or ~37.5% in the chromatogram 610 (WA—water after infusion with the structurally altered gas molecule 160) as compared to the chromatogram 620 (WB—the water before the infusion). The second peak in the 2.20 range on the X axis (Time) shows an increase in Abundance, (Y Axis) from 120,000 for WB to 155,000 for WA or ~22.6%. These differences indicate structural change of the water treated by the structurally altered gas molecule 160. Specifically, the differences indicate differences in H—O bond length, H—O—H bond angle, and decreasing influence of hydrogen bond with the increase in vapor release in the GC-MS sample chamber.

Thus, the FTIR plots 400 and 500, chromatography plots 600, 800, and 900 indicate that wave number, wave harmonic, angular frequency, angular wavelength, and angular period associated with the electromagnetic energy and geometry the structurally altered gas molecule are different than those resulting from any related electrolysis technique employed to produce hydrogen, ($H_2$), oxygen, ($O_2$), or any other molecule containing these elements.

Figure 10:
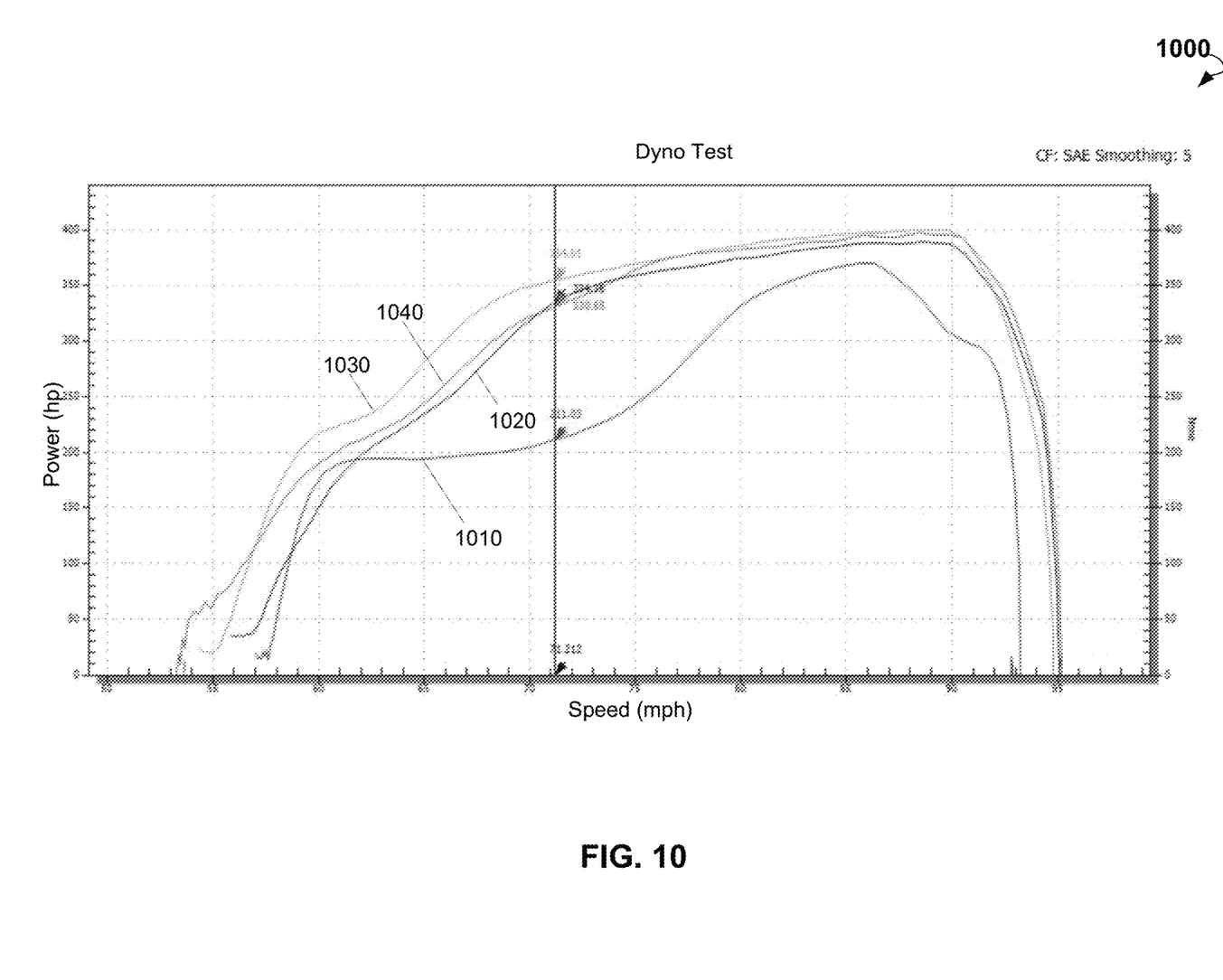
FIG. 10 is a diagram showing a dyno test analysis for a 110 octane fuel with and without structurally altered gas molecule infusion.

FIG. 10 is a diagram 1000 showing a dyno test analysis for a 110 octane fuel with and without structurally altered gas molecule infusion. The line 1010 represents the untreated fuel (i.e., a fuel not infused with the structurally altered gas molecule) and the lines 1020, 1030, and 1040 are runs of the dyno test on the same 110 octane fuel infused with the structurally altered gas molecule. All dyno tests for the 110 octane fuel infused with the structurally altered gas molecule were performed at the same temperature, pressure, and conditions as those used for the dyno test of the untreated fuel. During the research, there was an average of 37.9% increase in horsepower (hp) at the 71.212 miles per hour mark on the dyno tests with the 110 octane fuel infused with the structurally altered gas molecule.

The empirical evaluation of the emissions associated with the untreated fuel and the 110 octane fuel infused with the structurally altered gas molecule (via a smell test) showed a significant decrease in unburned hydrocarbons and other undesirable emissions and smells shown by the 110 octane fuel infused with the structurally altered gas molecule.

Figure 11:
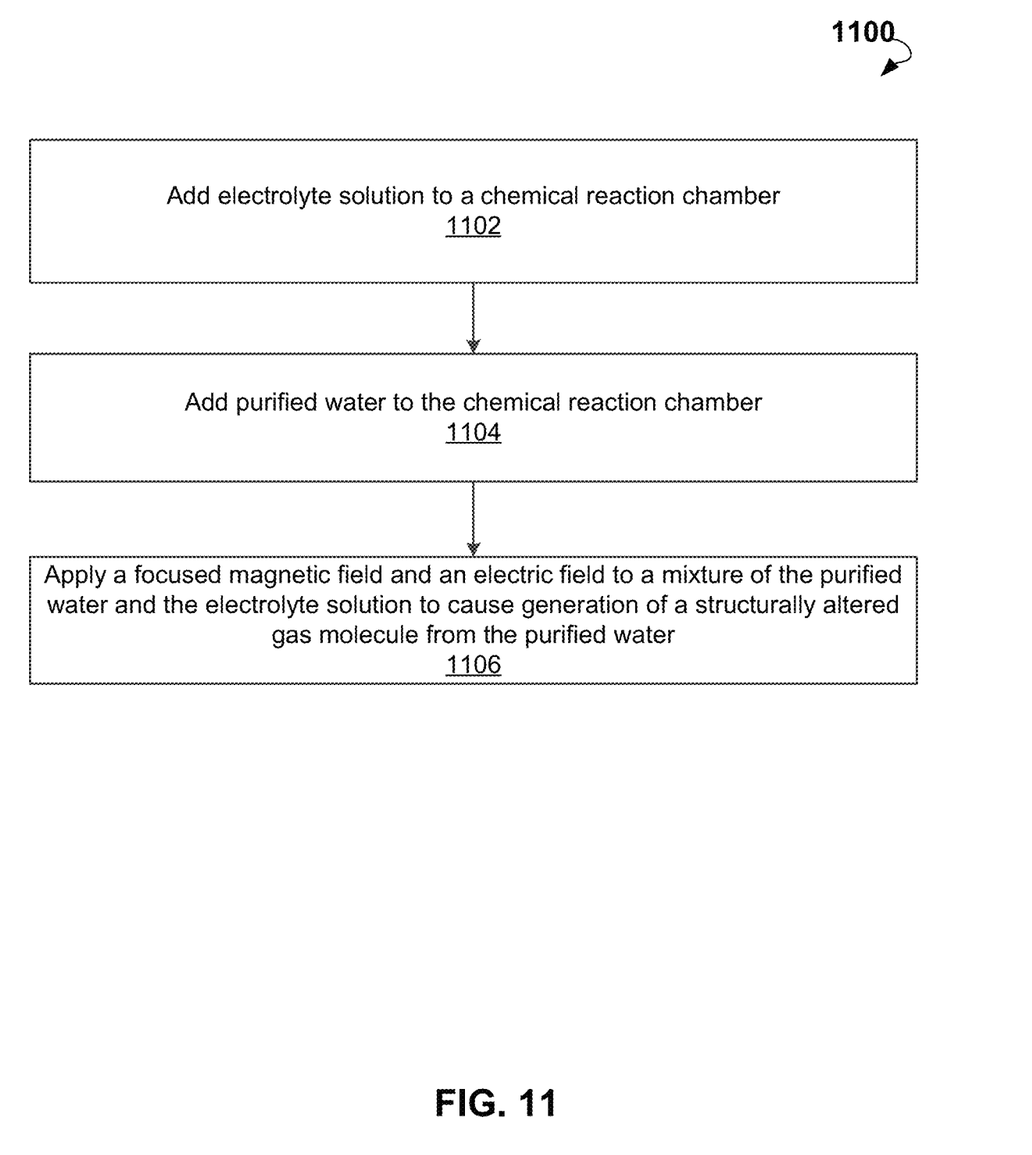
FIG. 11 is a flow chart showing a method for generating a structurally altered gas molecule from the water, according to an example embodiment.

FIG. 11 is a flow chart showing a method 1100 for generating a structurally altered gas molecule from water, according to an example embodiment. The method 1100 may commence, in block 1102, with placing an electrolyte solution in a chemical reaction chamber. The electrolyte solution can be made using a mixture of a hydroxide salt and an acid salt.

In block 1104, the method 1100 may proceed with adding purified water to the chemical reaction chamber. The temperature in the chemical reaction chamber can be from 60 degrees to 120 degrees in Fahrenheit. The pressure in the chemical reaction chamber can be from 1 atmosphere to 40 psig.

In block 1106, the method 1100 can proceed with applying a focused magnetic field and an electric field to a mixture of the purified water and the electrolyte solution to cause generation of the structurally altered gas molecule from the purified water. The structurally altered gas molecule can be a combination of two parts of hydrogen and one part of oxygen. A molecule of the structurally altered gas molecule has a hydrogen-oxygen-hydrogen bond angle between 94 degrees and 104 degrees and a bond length between 0.95 Angstrom and 1.3 Angstrom.

Thus, methods for generating a structurally altered gas molecule from water and a structurally altered gas molecule are disclosed. While the present embodiments have been described in connection with a series of embodiments, these descriptions are not intended to limit the scope of the subject matter to the particular forms set forth herein. It will be further understood that the methods are not necessarily limited to the discrete components described. To the contrary, the present descriptions are intended to cover such alternatives, modifications, and equivalents as may be included within the spirit and scope of the subject matter as disclosed herein and defined by the appended claims and otherwise appreciated by one of ordinary skill in the art.

What is claimed is:

1. A structurally altered gas molecule, the structurally altered gas molecule being a combination of two parts of hydrogen and one part of oxygen and produced from water by:
    placing an electrolyte solution in a chemical reaction chamber;
    adding purified water to the chemical reaction chamber; and
    applying a focused magnetic field generated by earth magnets and an electric field to a mixture of the purified water and the electrolyte solution to cause generation of the structurally altered gas molecule from the purified water, wherein:
        the structurally altered gas molecule has a hydrogen-oxygen-hydrogen bond angles between 94 degrees and 104 degrees and hydrogen-oxygen bond length between 0.95 Angstrom and 1.3 Angstrom; and
        a hydrogen bonding of the structurally altered gas molecule is neutralized.

2. The structurally altered gas molecule of claim 1 being produced with a mixture of a hydroxide salt and an acid salt as the electrolyte.

3. The structurally altered gas molecule of claim 1 having a density relative to a dry air of from 41.18% to 42%.

4. The structurally altered gas molecule of claim 1 being stable at a pressure exceeding 300 psig.

5. The structurally altered gas molecule of claim 1 having peak at 600 inverse centimeters in an infrared spectrum.

6. A solution of a structurally altered gas molecule and water, the solution having an oxidation/reduction potential of −50 to −360 millivolts and pH from 6.1 to 6.8, wherein the oxidation/reduction potential and the pH remain stable for at least 30 days after the solution is placed in closed insoluble vessel, the structurally altered gas molecule being a combination of two parts of hydrogen and one part of oxygen and produced from water by:
    placing an electrolyte solution in a chemical reaction chamber;
    adding purified water to the chemical reaction chamber; and
    applying a focused magnetic field generated by earth magnets and an electric field to a mixture of the purified water and the electrolyte solution to cause generation of the structurally altered gas molecule from the purified water, wherein:
        a temperature in the chemical reaction chamber is from 60 degrees to 120 degrees in Fahrenheit;
        a pressure in the chemical reaction chamber is from 1 atmosphere to 40 pounds per square inch gauge (psig); and
        the structurally altered gas molecule has a hydrogen-oxygen-hydrogen bond angles between 94 degrees and 104 degrees and hydrogen-oxygen bond length between 0.95 Angstrom and 1.3 Angstrom.

7. The structurally altered gas molecule of claim 1, wherein:
    a temperature in the chemical reaction chamber is from 60 degrees to 120 degrees in Fahrenheit; and
    a pressure in the chemical reaction chamber is from 1 atmosphere to 40 pounds per square inch gauge (psig).

8. The structurally altered gas molecule of claim 1, wherein the focused magnetic field is generated by earth magnets.

9. The structurally altered gas molecule of claim 1 when being dissolved in the purified water, forming a solution having an oxidation/reduction potential from −50 to −360 millivolts.

10. The structurally altered gas molecule of claim 9, wherein pH of the solution is from 6.1 to 6.8.

11. The structurally altered gas molecule of claim 10, wherein the oxidation/reduction potential and the pH remain stable for at least 30 days after the solution is placed in a closed insoluble vessel.

12. The structurally altered gas molecule of claim 1 when being dissolved in water having two parts per million (ppm) of total dissolved solids (TDS), causing the TDS to reduce to one ppm.

13. The structurally altered gas molecule of claim 1 when infused in water, causing a hydrogen bonding in the water to be neutralized.

* * * * *